United States Patent [19]

Hohmann et al.

[11] Patent Number: 4,710,233

[45] Date of Patent: Dec. 1, 1987

[54] METHOD AND APPARATUS FOR CLEANING, DISINFECTING AND STERILIZING MEDICAL INSTRUMENTS

[75] Inventors: Eugen Hohmann, Bensheim; Konrad Mund, Uttenreuth; Erhard Weidlich, Spardorf, all of Fed. Rep. of Germany

[73] Assignee: Siemens Aktiengesellschaft, Berlin and Munich, Fed. Rep. of Germany

[21] Appl. No.: 765,948

[22] Filed: Aug. 15, 1985

[30] Foreign Application Priority Data

Aug. 20, 1984 [DE] Fed. Rep. of Germany ....... 3430605

[51] Int. Cl.⁴ .............................................. B08B 3/12
[52] U.S. Cl. ......................................... 134/1; 134/18; 134/25.1; 134/25.4; 134/184; 204/130; 204/141.5; 204/155; 422/22
[58] Field of Search ................... 134/1, 18, 25.1, 25.4, 134/32, 95, 103, 169, 184, 171, 166 C; 204/130, 141.5, 155, 151; 422/22, 101

[56] References Cited

U.S. PATENT DOCUMENTS

| | | | |
|---|---|---|---|
| 3,007,478 | 11/1961 | Leonhardt et al. | 134/57 |
| 3,334,035 | 8/1967 | Dews et al. | 204/130 |
| 3,640,295 | 2/1972 | Peterson | 134/59 |
| 3,957,252 | 5/1976 | Storz | 134/1 |
| 3,975,246 | 8/1976 | Eibl et al. | 204/151 |
| 4,064,886 | 12/1977 | Heckele | 134/95 |
| 4,202,740 | 5/1980 | Stoner et al. | 204/130 |

FOREIGN PATENT DOCUMENTS 2332074 6/1977 France .
2094992 9/1982 United Kingdom ................... 134/1

Primary Examiner—Andrew H. Metz
Assistant Examiner—Sharon T. Cohen
Attorney, Agent, or Firm—Hill, Van Santen, Steadman & Simpson

[57] ABSTRACT

A method and apparatus for cleaning, disinfecting, and sterilizing medical instrument with a sequence of method steps performed in a single apparatus. The method steps include precleaning the instruments in a container containing a first fluid bath subjected to ultrasonic energy, subsequently emptying the first fluid bath from the container and replacing it with a second fluid bath containing a cleaning agent and a sodium chloride, fine cleaning and disinfecting the instruments by subjecting the second bath to ultrasonic energy and circulating the second bath through an electrolytic cell having a voltage applied to the electrodes to create anotic oxidation, then emptying the second bath and replacing it with a rinse bath, rinsing instruments while subjecting the rinse bath to an ultrasonic energy and circulating the bath through the electrolytic cell subsequently emptying the rinse bath, and drying the instruments by means of heated air.

27 Claims, 6 Drawing Figures

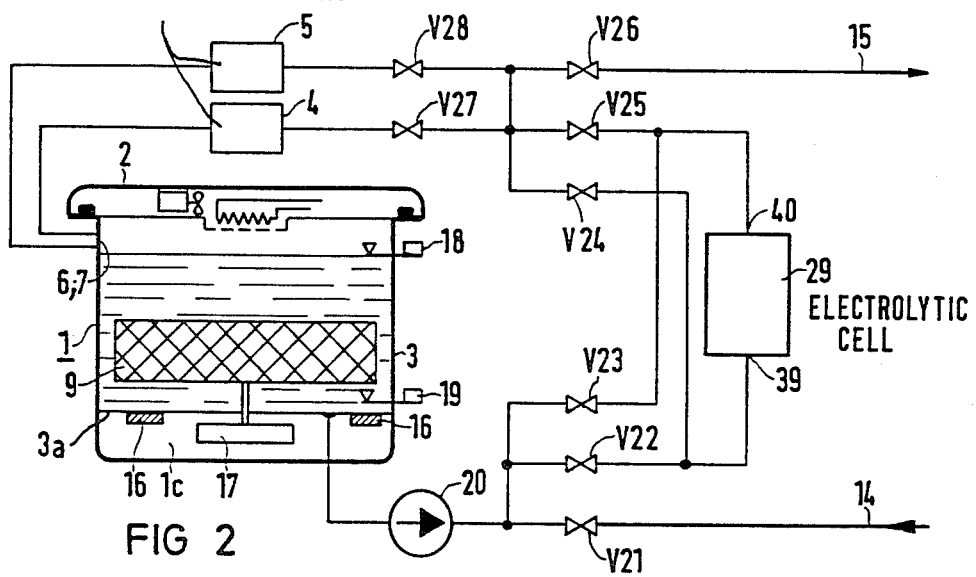
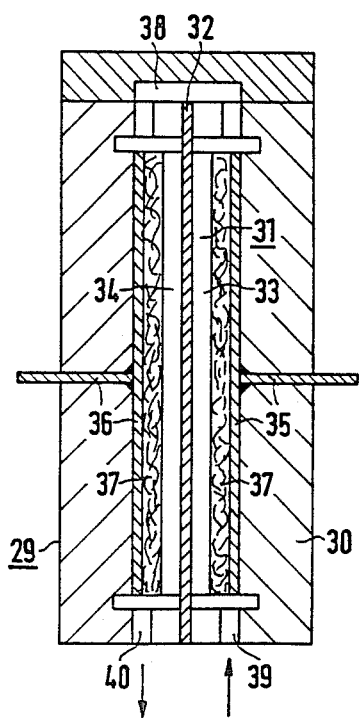

4,710,233

METHOD AND APPARATUS FOR CLEANING, DISINFECTING AND STERILIZING MEDICAL INSTRUMENTS

BACKGROUND OF THE INVENTION

The present invention is directed to a method and apparatus for cleaning, disinfecting and sterilizing medical instruments and particulary for cleaning disinfecting and sterilizing dental instruments.

From a hygenic point of view, the instruments such as forceps, tweezers, dental drills and etc. used in medical or respectively dental treatment should be germ-free. In order to meet this demand, it is normal to usually clean the instruments after their use by means of an ultrasonic cleaning system and examples of these systems are disclosed in U.S. Pat. Nos. 3,007,479 and 3,640,295. Then after cleaning, the instruments are disinfected or respectively sterilized in further or addtional work steps. The disinfection is usually carried out by a chemical solutions such as alchohols or fenols whereas hot air at about 180°-200° C. or superheated steam are utilized for the sterilization.

Instruments or part of instruments of non-metallic material, in particular, do not withstand these relatively high thermal stresses during sterilization. So-called gas sterilizers which utilize ethylene oxide are used in order to sterilize these sensitive instruments in a gentle way. A disadvantage of utilizing ethylene oxide is that it requires a relatively long-sterilizing time of a number of hours and ethylene oxide is highly toxic, explosive and, thus, a fire hazard. Thus, the use of ethylene oxide will require a relatively high cost for the necessary safety precautions.

SUMMARY OF THE INVENTION

The present invention is directed to a method of cleaning, disinfecting and sterilizing medical instruments which method avoids the disadvantage of known methods. In addition, the invention is directed to an apparatus with which the instruments can be faultlessly cleaned from a hygenic point of view in a relative short time and also be sterilized at the same time yet which apparatus is gentle on the instruments and does not create any environmental problems.

A significant advantage of the proposed measured is that the germ contaminated instrument no longer needs to be disinfected first in order to prevent infection of the operating personnel in a plurality of work steps and then subsequently cleaned manually or in a washing machine and then finally sterilized in a further working step. In accordance with the invention, the various steps can be executed automatically in a single apparatus in the following sequence: rough cleaning in an ultrasonic bath; fine cleaning and sterilizing in an ultrasonic bath with circulation of the fluid via an electrolytic cell; rinsing with a sterilized fluid in an ultrasonic bath; and drying by means of sterile heated air. The method is preferred in a single unit or apparatus having a first housing section containing a container for containing the various washing baths and a second housing section containing both electrical and hydraulic control elements, a cleaning agent dispensing means and a cleaning agent and sodium chloride dispensing means with a control system to enable running desired cleaning disinfecting and sterilizing steps.

Further objects and advantages of the invention will be apparent from the following drawings, descriptions and claims.

BRIEF DESCRIPTION OF THE DRAWINGS

FIG. 2 is a schematic illustration of the apparatus in FIG. 1 illustrating the various hydraulic circuits;

FIG. 3 is a longitudinal cross-sectional view of an electrolytic cell in accordance with the present invention;

DESCRIPTION OF THE PREFERRED EMBODIMENTS

Description of the Apparatus

Figure 1:
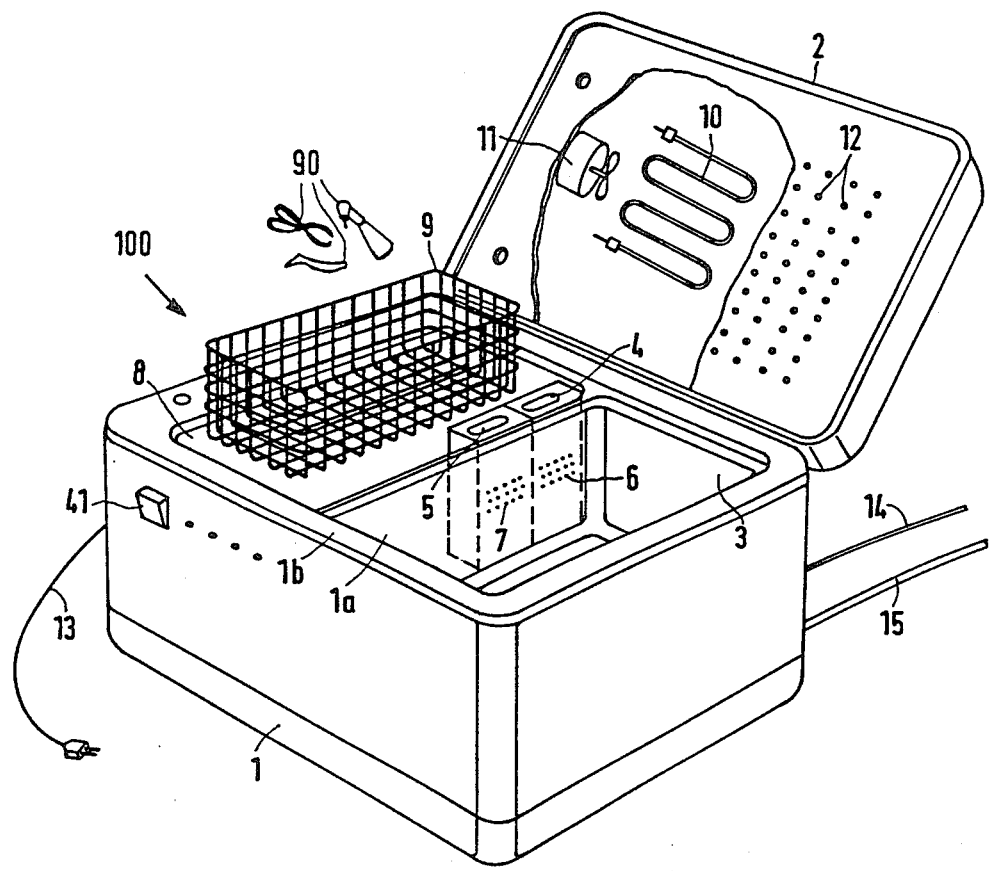
FIG. 1 is a perspective view with portions cut-away of an apparatus in accordance with the present invention.

The princples of the present invention are particularly useful when incorporated in a cleaning, disinfecting, and sanitizing apparatus generally indicated at 100 in FIG. 1. The apparatus 100 has a housing 1 having a box-shape which is subdivided into housing sections 1a and 1b which lies side by side. A tank-like container 3 is received in the housing section 1a and the housing section 1b has a cover 8. The housing 1 has a cover or lid 2 which is pivotably connected to one side and moves from a open position illustrated to a position which tightly seals the housing. The section 1b contains container 4 for the acceptance of a cleaning agent such as a surfactant as well as a second container 5 for the acceptance of a mixture of a sodium chloride (NaCl) and a surfactant. The two containers 4 and 5 are connected to the tank 3 through openings such as 6 and 7. The housing section 1b also contains various electrical and hydraulic components which are further illustrated in FIGS. 2 and 4 as well as an electrolic cell 29 which is shown in greater detail in FIG. 3.

To receive instruments 90, which may be scissors, tweezers, drill tools, etc. the apparatus includes a wire basket 9 which is placed in the container 3. The apparatus also includes a heating coil 10 which may be an infrared radiator as well as a miniature aerator or fan 11. The heating coil and fan are provided in the cover or lid 2 which also has a box-shape. As explained later, air heated by the coil 10 will be forced by the fan 11 into the tank 3 through openings 11 which are provided in the cover 2. The electrical supply for the electrical components is provided by an electrical line 13 that has a plug for connection to house current. In addition, the apparatus has a line 14 for receiving fresh water from a fresh water supply and a line 15 for discharging waste water to a sink or drain.

As illustrated in FIG. 2, the housing 1 beneath the section 1a has a third or lower housing section 1c. Ultrasonic oscillators 16 which are constructed in a standard fashion are secured in the lower housing section 1c immediately below the container and are mechanically coupled to a base or floor 3a of the container 3 so that fluid in the container 3 will be charged with ultrasonic energy from the ultrasonic oscillators 16. A vibrating or agitating means 17 is also provided in the housing section 1c and has a shaft which extends into the container and receives the basket 9 so as to provide a vibratory or agitating movement to the basket as desired. It is possible for the arm of the vibrating means 17 to terminate in a cradle which will receive the basket 9. The container also includes two level sensors which, for example, are in the form of electronic electric conductance sensors. These include an upper level sensor 18 and a lower level sensor 19. The floor or bottom 3a of the container also includes a drain which extends to a circulating pump 20 that is in the housing section 1b along with an electrolytic cell 29 and eight solenoid valves V21–V28.

Figure 5:
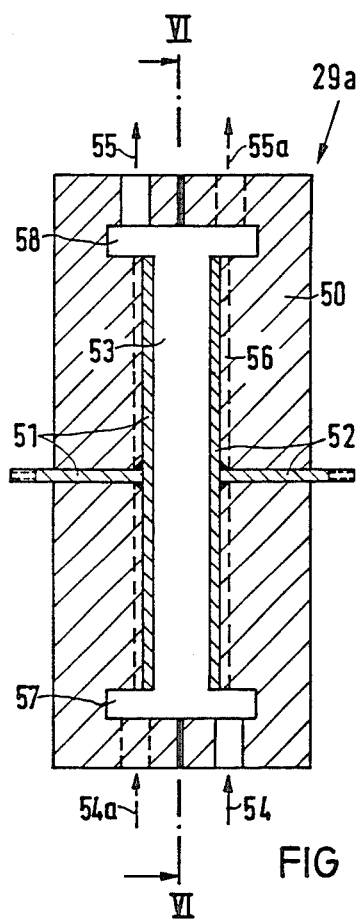
FIG. 5 is a longitudinal cross-section of an embodiment of the electrolytic cell.
Figure 6:
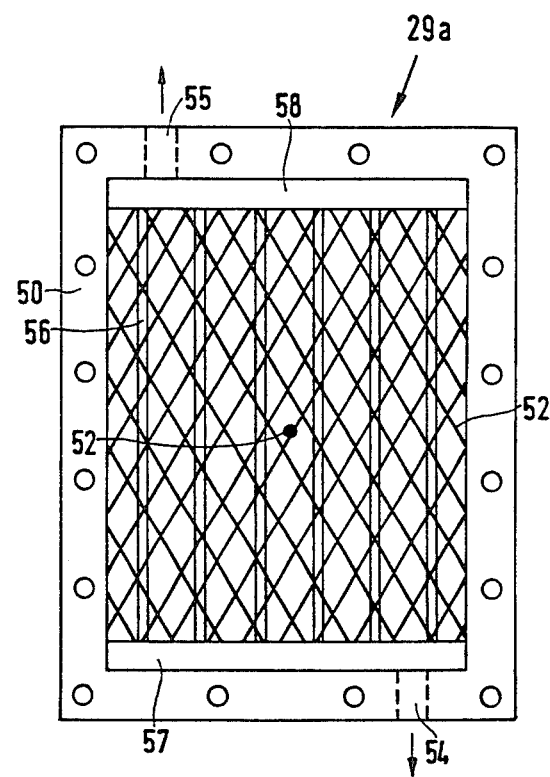
FIG. 6 is a view taken on lines VI—VI of FIG. 5.

The structure of the electrolytic cell 29 is illustrated in FIG. 3 with an embodiment 29a being illustrated in FIGS. 5 and 6. The cell 29 of FIG. 3 includes a housing 30 of an insulating material, which is rectangular in cross-section and has the dimensions of about 150 by 100 by 30 mm. The housing 30 contains a cavity 31, which is subdivided by a longitudinally stretched, ion-conducting membrane 32 into an anolyte chamber 33 and a catholyte chamber 34. The membrane is preferably composed of a sulfonated polytetrafluoroethylene and can be referred to as a cation exchange membrane. An anode 35 is disposed in the anolyte chamber 33 and a cathode 36 is disposed in the catholyte chamber 34. The anode and cathode are composed of the same material and preferably are composed of activated titanium. They can also be composed of platinum sheet which with one or more spot attached networks or gauze layers of platinum or of platinum iridium. Instead of the networks mentioned hereinabove, electrodes such as illustrated in FIGS. 5 and 6, which have a rib mesh of titanium or tantalum can also be used. These electrodes are coated with platinum black or platinum ruthenium oxide. When utilizing electrodes such as in FIGS. 5 and 6, the parting membrane between the anode and cathode can be eliminated.

It is also advantageous to employ chlorine-resistant, porous metals such as Raney platinum and porous titanium sponge. In addition, the electrodes can be of a sintered metals which may be coated with a precious metal catalyzer.

As illustrated in FIG. 3, in each of the two chambers 33 and 34 and adjacent the plate shaped electrodes, a turbulence grid 37 is provided. The turbulance grids 37 is intended to serve the purpose of placing the water stream into a turbulent condition. The turbulence grid 37 is made of a material which is a chemical-resistant fabric. For example, it can be made of polytetrafluoro ethylene. When utilizing the rib mesh electrodes such as illustrated in FIGS. 5 and 6, the turbulence grids 37 can be eliminated. The necessary turbulation of the flowing water is already achieved by the geommetrical shape of the rib mesh of the electrodes of FIGS. 5 and 6.

The anolyte chamber 33 is connected by a channel 38 to the catholyte chamber 34. Thus, the fluid flowing into an inlet port 39 which is indicated by the arrow passes through the anolyte chamber 33, and then through the channel 38 into the catholyte chamber 34 to be discharged through a discharge channel or port 40.

An embodiment of the electrolytic cells is generally indicated 29a in FIGS. 5 and 6. The cell 29a has an outer shape and electrode structure which is generally the same as the cell 29 of FIG. 3. For example, two electrodes 59 and 52 which can have a DC current applied thereto are disposed at a distance of 0.5 to 5 mm in a housing 50 of insulating material. In contrast to the cell 29 however, the cell 29a has no membrane to subdivide the cavity or flow through chamber 53, which extends between the electrodes 51 and 52. Accordingly, an intake channel 54 and a discharge channel 55 are disposed on opposite ends of the housing 50. In order to receive a more uniform flow of the fluid through the cell, it is expedient, as shown in broken lines to provide a plurality of intake and discharge channels 54a and 55a. In order to improve the efficiency is also advantageous to provide flowthrough or, respectively aeriations channels 56 between the electrode and the housing 50. As best illustrated in FIG. 6, these channels 56 extend in the direction of the flow. These channels can also be designed as a honeycomb-like and is also conceivable and within the frame work of the invention to place the electrodes at a distance relative to the housing wall by means of some other suitable measure. Advantageously, for an optimum flow-through, it is also desirable to provide a distributor chamber 57 adjacent the inlet port 54 and a distributor chamber 58 adjacent the outlet port 55. These distributor chambers 57, 58 extend over the width of the electrodes as illustrated.

Even though the efficiency of the single chamber cell 29a is not as good as the cell 29 having the divided chambers, the structure of the single chamber cell is considerably simpler and the cost for the hydraulic circuit associated therewith which is described hereinafter, will be less. Given employment of the divided cell 29 with a highly calciferous water with the hardness of greater than 10° dH, it is recommendable to place an ion exchanger the system before the cells 29 in order to avoid lying deposits on the partition or membrane.

Figure 4:
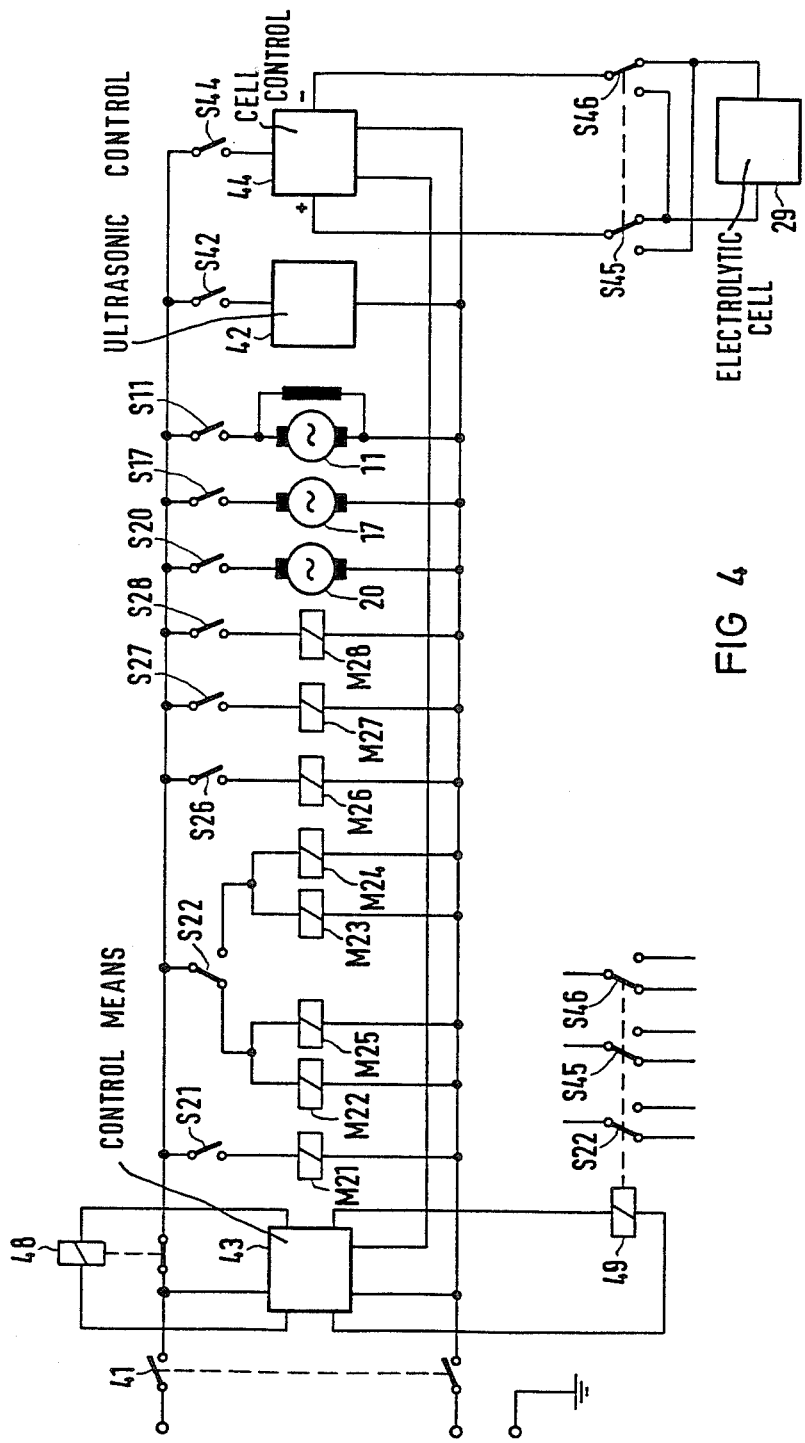
FIG. 4 is an electrical circuit diagram for the apparatus according to FIG. 1.

As illustrated in FIG. 4, the electrical system which is also located in the chamber 1b includes a plurality of switches such as S21, S22, S26, S27, S28 which control applying electrical power to solenoids M21–M28 for the solenoid valves V21–V28. In addition, electrical system includes the switch S20 for the motor of the pump 20, a switch S17 for the motor of the oscillating or agitating means 17 and a switch S11 for the motor of the fan 11. An ultrasonic electronic means 42 has a switch S42 while a control means or power means 44 for the electrolytic cell such as 29 has a switch S44. In addition to above, overall control means 43 are illustrated and controls the actuation of the various switches at the desired time in response to the sensed conditions.

Description of the Method

To operate the device or apparatus 100, the contaminated instruments 90 are placed in a wire basket 9 and this in turn is placed in the initially empty cleaning container 3. A premeasured amount of powdery or fluid surfactant or cleaning agent is introduced either manually or via an external doser, which can be positioned in the proximity of the apparatus 100, into the container 4. In a similar manner, a mixture of the cleaning agent and sodium chloride is placed in the container 5. It should be noted that the container 4 and 5 are dispensing means and that these steps can be reversed if the following described sequence or steps is modified.

After placing the cleaning agent and the mixture in the respective containers or dispensing means, the cover 2 is closed and the cleaning, disinfecting and sanitization process or method can begin.

By pressing a start button 41 (FIGS. 1 and 4) the control means 43 will close switches 21 and 27 as well as position the switch 22 into position illustrated in FIG. 4 so that the solenoids M21, M22, M25 and M27 are actuated to open valves 21, 22, 25 and 27. In this condition, water from feed line 14 (FIG. 2) passes through the open valves V21, V22, the electrolyte cell 29, the valves V25 and V27 into the container 4 which has the cleaning agent. The water stream washes the cleaning agent that was situated in the container 4 into the container 3. After the desired or required filling level has been reached, which will be indicated by the sensor 18, the water feed is interrupted by opening the switches S21 and S27 to close the valves V21 and V27. Simultaneously, the switch S17 is closed to energize the agitating unit 17. This causes the basket 9 and the instruments contained therein to be shook in the liquid bath of the container 3 with the movement being either a vertical or horizontal oscillating motion.

When the ultrasonic control or electronics 42 is switched on by means of closing the switch S42 of FIG. 4, the ultrasonic transducer 16 (FIG. 2) are placed in oscillation and the fluid situated in the container 3 is then charged with ultrasonic energy. A rough cleaning will begin. It is proven favorable for the cleaning effect when the ultrasonic frequency lies below 35 kHz and roughly at 30 kHz in that the Rf power amounts to at least 80w/1 for the bath content. The surfactant or cleaning agent employed should have a low lather action. The cleaning effect is considerably promoted by the motion generated by the agitating means 17. The rough cleaning will require a time T1 of between 3 and 5 minutes. After the time T1 has past, the control means 43 will open the switches S17 and S42 to shut off the oscillating means 17 and the ultrasonic control 42. To remove the contents of the container 3, control means 43 also closes the switch S28 to start the pump 20 and the switch S26 to actuate the solenoid M26 to open the solenoid valves V26 so that the contents can be pumped by the pump 20 through the valve V22 to the electrolytic cell 29, the valve 28 and the valve 27 to the discharge line 15. At the same time, the control means 43 closes the switch S44 so that the control means 44 for the cell 29 applies a voltage to the electrodes of the electrolytic cell 29. With the current density lying in the range of $50mA/cm^2$ through $100mA/cm^2$ of electrode area, an electrolytic dissaociation will occur which would kill the majority of the germs contained in the fluid passing through the electrolytic cell 29. When the lower filling level is reached which will be indicated by the sensor 19, the signal created by the sensor 19 will be received by the control means 43 which will open the switches S26 to close the valve V26, the switch S20 to stop the circulation pump 20, and switch S44 to shut off the electrolytic cell 29.

The control means 43 will then initiate a filling operation by closing the switches S21 and S28 to open the valves V21 and V28 as well as maintaining the switch S22 in the positions so that the valves V22 and V25 are remain open. In this arrangement, water in the line 14 will flow through the valves V21, V22 the cell 29, the valve V25 and the valve V28 into and through the container 5. As a water flows through the container 5 it will entrain the mixture of sodium chloride and cleaning agent and carried it into the container 3. When the container 3 is filled which will be indicated by the sensor 18 sending a signal to he control means 43, the control means will open the switch S21 to close the valve 21.

When the control means 43 receives the signal from the sensor 18, it will initiate the fine cleaning and sterilization step. This is accomplished by the control means 43 closing the switches S42 to apply power to the ultrasonic control means 42 to start applying ultrasonic energy to the fluid and also closing the switch S44 for the cell control means 44 so that a voltage is applied to the electrodes of the cell 29. In addition, the switch S20 is closed to start the pump 20 so that the fluid in the container 3 is pumped by the pump 20 through a circuit of the valve V22, the cell 29, the valve 25, the valve 28 and back into the chamber 3. Thus, the bath is continually circulated through the electroylytic cell 29 for a definite fine cleaning time T2 which likewise is only for a few minutes. The characteristic feature of the method lies in the circulation. The germs contained in the flowing fluid are mainly killed in the anolyte chamber of the cell. The killing process is based on the effect which is produced by the electrolytic disassociation. In detail, these are the direct oxidation of the germs due to electron withdrawal given contact with the anode surface of the electrode, an indirect oxidation of the germs due to nascent oxygen, oxidation of the germs due to free chlorine, and denaturization of the germs due to the acid content of the solution given pH values in the region of pH2. As tests have shown, a physiological table salt solution loaded with $10^6$ germs/ml of a species of bac. subtilis in spore form was made germ-free in less than 3 minutes. A physiological table salt solution inoculated with spore earth with amount of $10^4$/ml was sterile after five minutes. The following operating conditions were utilized: bath content 1.5 liters, circulation 600 ml/minute, electrode area $100cm^2$, and current density 100 $mA/cm^2$. After flowing through the analyte chamber, the fluid proceeds into the catholyte chamber. Due to the alkalescence in combination with hydrogen generation, the calcium carbonate in hard water is precipitated. This side effect will promote a fine cleaning.

After the execution of the fine cleaning and sterilization, which occurs after the time T2, the switches S28 and S42 are opened to close the solenoid valve 28 and to shut off the ultrasonic electronic 42. In addition, the switch S26 is closed to open the valve V26 so that continual pumping of the solution by the pump 20 will discharge the fluid of the container 3 through the electrolytic cell 29 and into the discharge line 15.

After completion of emptying the container of the fine cleaning and sanitizing solution which will be indicated by the sensor 19, a rinse phase will begin. In the rinse phase, the liquid in the container is again subjected to the ultrasonic energy and the fluid is continuously circulated through the electrolytic cell 29. However, the cell 29 is now operated with the reduced current density of a range of about $5mA/cm^2$ through $20mA/cm^2$. This current density is adequate in order to kill germs which may have been brought in via the line water. The rinsing phase thus occurs with practically sterile fluid. After conclusion of the rinsing phase which is conducted for a time T3 which amounts to two to three minutes, the bath in the container 3 is again emptied into the discharge by being pumped out.

The next step is the drying process. The control means 43 closes the switch Sll to apply power to the heating coil 10 and to energize the motor 11 so that heated air generated by the heating coil 11 is introduced into the container by the fan 11 through the openings 12 and is brought to the goods to be sterilized. In addition, the switch S17 is closed so that the agitating or oscillating units 17 will operate during the drying process. The drying process is limited to a time T4 which is only a few minutes.

The overall control of the method sequence can occur by through a circuit diagram of FIG. 4 with the control means 43 which is preferably formed by a microprocessor controlling the program execution. The signals which are required from the lever sensors 18 and 19 serve as input variables. When the electronic electrical conductance probes are employed as level sensors, they not only can determine the level which is occurring but from the electrical conductance of the fluid they can also monitor the amounts of the cleaning agent or, respectively, sodium chloride which is present. The dosing of the sodium chloride and the cleaning agent can also be obtained from a cell voltage of the electrolytic cell 29 and from the cell current.

The electrolytic cell 29 receives its voltage from the control electronics or means 44 which receives power when the switch S44 is closed.

In case of a malfunction, i.e. when the prescribed limit values of the input variables are exceeded, a relay 48 interrupts the sequence process. In addition, the relay 48 will actuate an acoustical signal and an optical malfunction display for example to draw attention to the function and operating errors.

The switching of the contacts S22, S45 and S46 occurs by means of a relay 49 after every program execution. Given, for example, odd number program execution, the relay 49 can be in an active position and for an even number of program executions it can be in an idle position. The relay 49 thus will switch the various switches S22, S45 and S46 from the positions illustrated to the unillustrated position. For example, the switch S22 opens or causes the valves 22 and 25 to be held in an open position when it is in the position illustrated. When switched to the opposite position, the valves V22 and V25 are closed but the valves V23 and V24 are then held open. In addition, when switched to the position which opens the valve V23 and V24, the switches S45 and S46 will move to a position to reverse the polarity of the electrodes 35 and 36. As can be seen from FIG. 2, if the valves V23 and V24 are closed and the valves V22 and V25 are opened, fluid will flow through the valve V22 into port 39 of the cell 29 the out port 40 through the valve V25. However, with the valves V22 and V25 closed and the valves V23 and V24 opened, fluid from the pump 20 will flow through the valave V23, the port 40 through the cell 29 and out the port 39 and through the valve V24. However, since the electrode 35 and 36 have had a pole reversal i.e. the previous anode 35 became a cathode and the previous cathdoe 36 became an anode, the fluid will still go into the anolyte chamber first and then pass into the catholyte chamber. The poll reversal and the reverse flow has a particular advantage when operating with hard water since the calcium carbonate not only precipitated in the fluid but also will build up as a layer on the cathode electrode. Due to the switch over, a back formation occurs and is also referred to as a regeneration of the cell. A constant function of the cell is thus guaranteed.

The replenishment of the cleaning agent and the sodium chloride can occur from larger supply reservois by utilizing dosage means. A further simplification can likewise be undertaken with respect to the electrical structure wherein the solenoid valves V22, V23, V24 and V25 for switching the flow direction in the electrolytic cell can be reduced in number by employing two-way valves.

As already mentioned, the outlay of the control of the agent flow can be greatly simplified utilizing electrolytic cell 29a of FIGS. 5 and 4. This is due to elimination of the reversing flow directions. When considering the fundamental circuit diagram of FIG. 2, it will be readily apparent that the valves V22 through V25 as well as the line sections to and from the valves V23 and V24 can be eliminated. When considering the fundamental circuit diagram of FIG. 4, it would also be obvious that the switch S22 would not be necessary. The remaining switches would be retained.

The control means 43 as mentioned above can be a microprocessor. To accomplish the various functions, it merely needs to follow a program of closing the various switches for a given time length such as the time T1 during the rough cleaning operation then changing the switch setting for the removal of the rough cleaning fluid with the time for the removal being controlled or determined by the input of the level sensors. Then starting the second filling operation for the fine cleaning and disinfecting cycle which filling operation will be terminated when the upper level sensor indicates the desired level operating the device in the fine cleaning and disinfecting cycle for the time length T2, starting the draining of the liquid which will be indicated as being completed by the lower level sensor 19 then starting the filling of the rinsing liquid, which will end from a signal created by the upper level sensor 18, operating the rinsing cycle for the time limit T3, then operating the draining of the rinsing liquid which completion will be determined by the lower level sensor 19, and subsequently starting the drying cycle for the time limit T4. As mentioned, while a microprocessor can be utilized various timing mechanisms with switching inputs can also be utilized.

Although various minor modifications may be suggested by those versed in the art, it should be understood that we wish to embody within the scope of the patent granted hereon all such modifications which reasonably and properly come within the scope of our contribution to the art.

We claim:

1. A method for cleaning, disinfecting and sterilizing a medical instruments, said method comprising the steps of:

providing a container for receiving a fluid bath, and introducing the instruments into the container;
   filling the container with a fluid and a cleaning agent to form a first fluid bath receiving the instruments to be cleaned;
   precleaning the instruments by subjecting the first fluid bath in the container to ultrasonic energy for a period of time T1;
   emptying the first fluid bath from the container and filling said container with a second fluid bath containing both a cleaning agent and sodium chloride;
   fine cleaning and sterilizing the instruments in the second fluid bath for a time period T2 by subjecting the second of fluid bath to ultrasonic energy, and circulating the second fluid bath through an electrolytic cell operating on a voltage to create an electrolytic disassociation therein;
   emptying the second fluid bath from the container and filling said container with a rinsing fluid bath;
   rinsing the instrument for a time period T3 by subjecting the rinsing bath to the ultrasonic energy and circulating the rinsing bath through the electrolytic cell;
   subsequently emptying the rinsing bath; and
   drying the instruments for a time period T4 by subjecting the instruments to heated air.

2. A method according to claim 1, wherein each of the step of removing the fluid baths from the container includes passing the fluid bath through the electrolytic cell to a discharge; and at least during the discharging of the first fluid bath, operating the electrolytic cell to disinfect the fluid as it is being discharged.

3. A method according to claim 1, wherein each of the steps of filling the container includes passing the fluid through the electrolytic cell before the fluid enters the container and at least during the step of providing the rinsing fluid bath, operating the electrolytic cell to disinfect the rinsing fluid.

4. A method according to claim 3, wherein each of the steps of removing the fluid bath includes removing the fluid of the bath through the electrolytic cell and operating the cell during at least the step of removing the first fluid bath to disinfect the first fluid bath prior to discharge into a waste line.

5. A method according to claim 1, wherein the step of filling the container with the first bath includes passing the water through a dispensing means for the cleaning agent and the step of filling the container with the second bath includes passing the fluid through a dispensing means for a mixture of the cleaning agent and sodium chloride.

6. A method according to claim 1, wherein introducing the instruments introduces the instruments in a basket and the container includes means for shaking the basket during each of the cleaning and rinsing steps.

7. A method acording to claim 1, wherein the duration of each of the filling and emptying steps is determined by sensing means sensing an upper and lower liquid level in the container.

8. A method according to claim 7, which further includes controlling the various steps from sense data, said means for sensing the liquid level in addition sensing the electrical conductance of the fluid.

9. A method according to claim 1, wherein the electrolytic cell during the emptying of the first fluid bath and during the cleaning and disinfecting are operated with a current density of a range of 50mA–100mA/cm$^2$ for the electrode area of the electrodes of the cell and during the rinsing phase are operated at a reduced density preferably in a range of 5mA–20mA/cm$^2$ for the electrode area.

10. An apparatus for cleaning, disinfecting and sterilizing medical instruments, said apparatus comprising a housing, a container positioned in the housing for receiving the instruments to be processed and for receiving a fluid bath, an electrolytic cell, drying means for drying the instruments in the container, an ultrasonic means having at least one ultrasonic transducer coupled to the container for applying ultrasonic energy to a fluid in the container, hydraulic control means for controlling the filling and draining of the container, and including lines extending between the container and the electrolytic cell, and an electrical control means for controlling the operation of the ultrasonic means, the electrolytic cell, the drying means and the hydraulic circuit.

11. An apparatus according to claim 10, wherein the housing is subdivided into housing sections with the first section containing the container, a second section adjacent the first section, and containing the electrical means, the hydraulic control means, the electrolytic cell, dispenser means for cleaning agents and sodium chloride and a third section beneath the container containing the ultrasonic transducers.

12. An apparatus according to claim 11, which further includes a cover engaged on the housing to seal the container, said cover including the drying means.

13. Apparatus according to claim 12, wherein the drying means includes a heating device and a fan for blowing air from with the heating device through apertures in the cover and into the container.

14. Apparatus according to claim 10, wherein the control means includes liquid level sensors for determining the upper and lower filling levels of the fluid bath in the container.

15. Apparatus according to claim 10, wherein the ultrasonic means is capable of operating at a frequency 35 kHz with a power of at least 80W/1 of liquid in the container.

16. An apparatus according to claim 10, wherein the hydraulic control means and the electrical control means includes a changeover means to enable changing voltage polarity of the electrodes of the electrolytic cell and for changing the direction of flow of the fluid through the cell after predetermined operational steps to enable rejuvenating the cell by removing deposits on the electrodes.

17. An apparatus according to claim 10, wherein the electrolytic cell is composed of a housing having an elongated chamber containing an anode and a cathode separated by an ion transmissive partition to form an anoltye chamber adjacent the anode and a catholyte chamber adjacent the cathode said anolyte and catholyte chambers being interconnected at one end of the housing by a flow channel, said housing having inlet and outlet ports disposed at an end opposite said channel, the inlet port being in communication with the anolyte chamber and outlet port being in communication with the catholyte chamber.

18. An apparatus according to claim 17 wherein the ion transmissive partition is a cation exchange membrane having a flow resistance which is high in comparison to the flow resistance in the anolyte and catholyte chambers.

19. An apparatus according to claim 17, wherein the electrodes are composed of activated titanium preferably in the form of a network.

20. An apparatus according to claim 19, wherein the electrodes are activated with precious metal.

21. An apparatus according to claim 17, wherein the electrodes contain an electro-catalizer.

22. An apparatus according to claim 17, wherein the effective electrode area is between 50 and 250cm$^2$.

23. An apparatus according to claim 10, wherein the electrolytic cell is composed of housing having elongated cavity forming a flow through chamber with two electrodes spaced along the surface thereof, said flow-through chamber adjacent each of the electrodes having flow through channels extending parallel to the direction of flow through the housing.

24. An apparatus according to claim 23, wherein the electrodes are composed of an activated titanium preferably in a rib mesh configuration.

25. An apparatus according to claim 23, wherein the electrodes are activated with precious metals.

26. An apparatus according to claim 23, wherein the electrodes contain an electro-catalyzer.

27. An apparatus according to claim 23, wherein the effective electrode area amounts to between 50 and 250 cm$^2$.

* * * * *